United States Patent [19]

Furuhata

[11] Patent Number: 5,078,145
[45] Date of Patent: Jan. 7, 1992

[54] ULTRASONIC DIAGNOSTIC DEVICE
[75] Inventor: Hiroshi Furuhata, Kasukabe, Japan
[73] Assignee: Nichimen Corporation, Saitama, Japan
[21] Appl. No.: 516,777
[22] Filed: Apr. 30, 1990
[51] Int. Cl.$^5$ .............................................. A61B 8/00
[52] U.S. Cl. ................................. 128/660.07; 128/916
[58] Field of Search ...................... 128/661.07–661.10, 128/660.07, 916; 73/620–621, 625–626; 364/413.25

[56] References Cited

U.S. PATENT DOCUMENTS

| Re. 30,397 | 9/1980 | King | 128/916 X |
|---|---|---|---|
| 3,222,740 | 12/1973 | Hokanson | 128/661.09 |
| 4,341,120 | 7/1982 | Anderson | 128/916 X |
| 4,492,119 | 1/1985 | Dulopa et al. | 73/621 |

FOREIGN PATENT DOCUMENTS 56-70757 6/1981 Japan .
2-124148 5/1990 Japan .

OTHER PUBLICATIONS

Brinkley, J. F. et al., "Ultrasonic Three-Dimensional Imaging and Volume from Sector Scans", UTs in Med and Biol., vol. 4, pp. 317–377.

Primary Examiner—Francis Jaworski
Attorney, Agent, or Firm—Burns, Doane, Swecker & Mathis

[57] ABSTRACT

An ultrasonic diagnostic device is disclosed in which ultrasonic pulses are transmitted for a subject body in changing the position and direction of a probe, and a plurality of two-dimensional tomographic image signals obtained by detecting the reflected pulses are synthesized to form a three-dimensional image. A signal for identifying the position in three-dimensional coordinates based on the position and direction of the probe at the time of detection is given to individual picture element signals composing in the detected two-dimensional tomographic image. A plurality of two-dimensional tomographic image signals having identified positions in three-dimensional coordinates are obtained by the similar processes to described in the above in changing the position and direction of the probe, and a plurality of the picture element signals having the same coordinates are addition-averaged and are stored in the memory area corresponding to the coordinates in the three-dimensional memory. With the arrangement as described in the above, the three dimensional image can be formed which is not influenced by hardness in the tissue etc.

7 Claims, 6 Drawing Sheets

ULTRASONIC DIAGNOSTIC DEVICE

BACKGROUND OF THE INVENTION

1. Field of the Invention

The present invention relates to an ultrasonic diagnostic device and, more particularly to an ultrasonic diagnostic device which can display a tomographic image or a three-dimensional image of a specific region from information obtained by scanning a living body; further to an ultrasonic diagnostic device which can offer an accurate two-dimensional or three-dimensional image by synthesizing a plurality of tomographic image signals having different positions or directions.

2. Description of the Prior Arts

Figure 7:
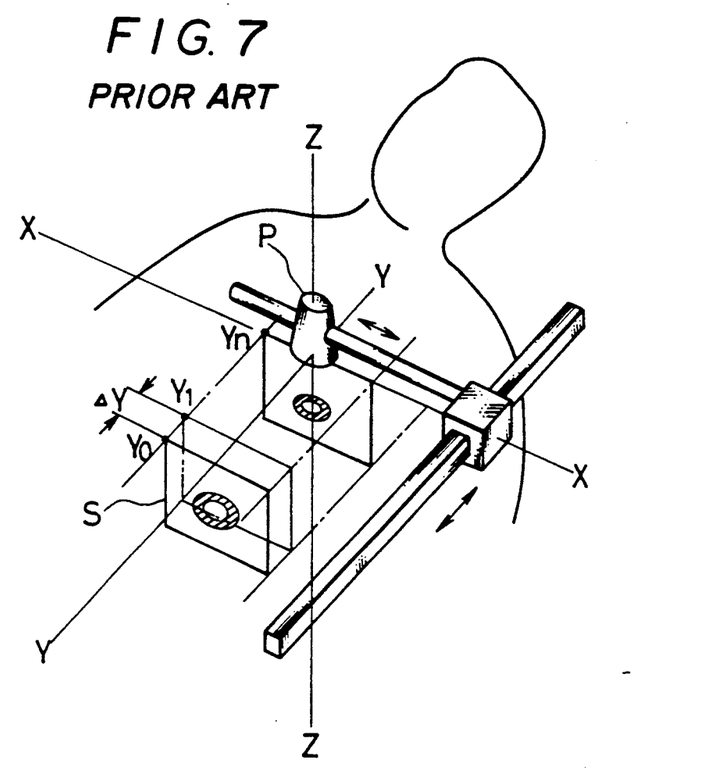
FIG. 7 shows a principle of the formation of a tomographic image taken along an arbitrary cross section from a plurality of two-dimensional tomographic images.
Figure 8:
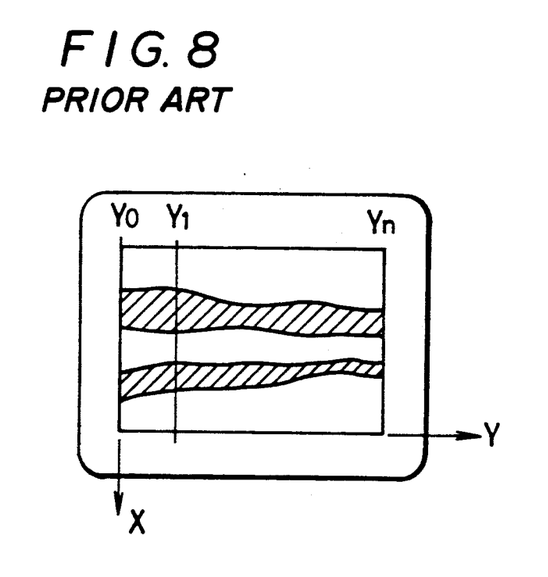
FIG. 8 shows an example of a tomographic image produced by the principle shown in FIG. 7.

There is a well-known ultrasonic diagnostic device in which the surface of a living body is irradiated with ultrasonic waves for observing the inner part of the living body and a tomographic image of the living body or an image on a sectional plane which makes a right angle with the scanning sectional plane in a three-dimensional meaning is obtained by detecting the reflected waves from the living body. Among the devices of this kind, as shown in FIG. 7, a probe P is scanned in an X axis direction for a living body, and the obtained tomographic image signal of an X-Z cross section S is stored in an image memory, and then the probe P is moved by a specified small distance $\Delta Y$ in a Y axis direction and the probe is again scanned in the X axis direction and another tomographic image signal is obtained in the similar way as mentioned in the above. If a plurality of these two-dimensional tomographic image signals obtained by repeating the process described in the above are transformed to the signals on three-dimensional coordinates, they, as a whole, form a signal showing a three-dimensional image; therefore it is possible to display a tomographic image taken along an arbitrary cross section as shown in FIG. 8. (See Japanese Laid-open Patent Publication No. Sho 56-70757.)

In this kind of devices, a probe is scanned only once in a specific region (hereinafter referred to as a watch point), so that only one image signal is obtained for a watch point. Ultrasonic waves, in their nature, are strongly reflected by a hard tissue like a bone and also permeate diffracting around it; therefore, when there is a tissue which reflects ultrasonic waves in the vicinity of a watch point, a complete image is not always obtained.

SUMMARY OF THE INVENTION

A main object of the present invention is to provide an ultrasonic diagnostic device of a new type in which the fault of an image obtained with a conventional ultrasonic diagnostic device is solved.

Another object of the present invention is to provide an ultrasonic diagnostic device of a new type in which an image of a subject body is synthesized based on a plurality of image signals obtained by scanning the subject body a plurality of times from different directions; therefore it is made possible to obtain an image of the subject body which is not influenced by the hardness of the tissue of the subject body, etc.

Other objects of the present invention will become apparent from the following descriptions and the appended claims with reference to the accompanying drawings.

BRIEF DESCRIPTION OF THE DRAWINGS

FIG. 1 (a), (b), (c) and (d) are illustrative representations illustrating the coordinates of a specific region of a subject body when the scanning is performed in changing the position and direction of a probe in reference to the subject body;

DETAILED DESCRIPTION OF THE PREFERRED EMBODIMENTS

The explanation on the embodiments according to the present invention will be given in the following.

According to the present invention, a specific region (watch point) of a subject body is scanned from a plurality of different positions and directions to obtain two-dimensional tomographic image signals and to convert these signals to an image signal on three-dimensional coordinates. The explanation on the coordinates of a watch point T detected on a probe scanning surface will be given concerning a case where a vibrator surface of a probe is situated at distances dx, dy and dz from the origin in the directions of X, Y and Z axes, and the probe vibrator surface is inclined by angles $\Phi$ for X axis, $\theta$ for Y axis and $\Psi$ for Z axis.

Figure 1A:
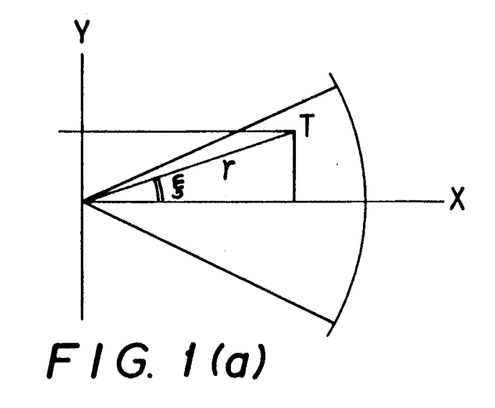

When the vibrator surface of the probe (hereinafter referred to as simply probe) is put at the coordinate origin, a reference scanning plane of the probe is set on an X-Y plane and a reference scanning direction is set in an X axis direction, the coordinates of the point T are $$X = r \cos \xi$$

$$Y = r \sin \xi$$

$$Z = 0$$

wherein r is the distance (depth) from the probe to the watch point T, and $\xi$ is the deviation angle of the watch point T with respect to a reference scanning direction.

Figure 1B:
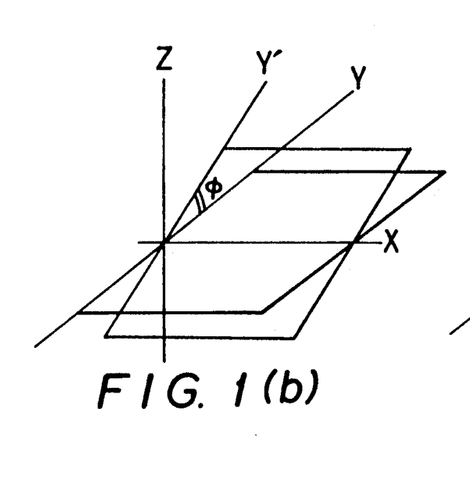

When the probe is rotated around the X axis by an angle $\Phi$, (namely, the reference scanning surface is rotated around the X axis by an angle $\Phi$) as shown in FIG. 1 (b), the coordinates of the point T are expressed by the following equations.

$$X = r \cos \xi$$

$$Y = r \sin \xi \cdot \cos \Phi$$

$$Z = r \sin \xi \cdot \sin \Phi$$

Figure 1C:
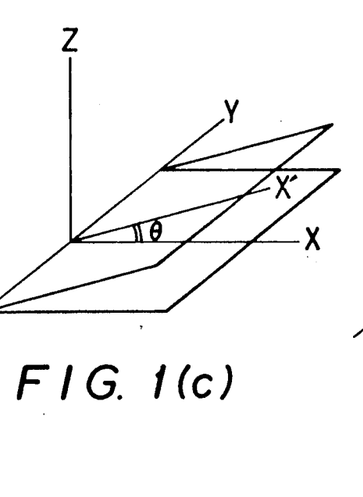

When the probe is rotated around a Y axis by an angle $\theta$, (namely, the reference scanning surface is rotated around a Y axis by an angle $\theta$) as shown in FIG. 1 (c), the coordinates of the point T are expressed by the following equations.

$$X = r \cos \xi \cdot \cos \theta$$

$$Y = r \sin \xi$$

$$Z = r \cos \xi \cdot \sin \theta$$

Figure 1D:
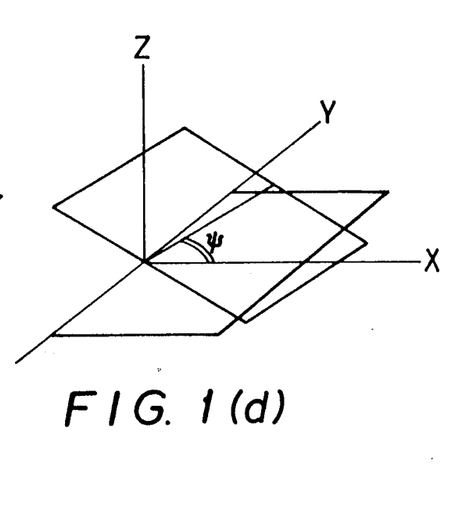

When the probe is rotated around a Z axis by an angle $\Psi$, (namely, the reference scanning surface is rotated around a Z axis by an angle $\Psi$) as shown in FIG. 1 (d), the coordinates of the point T are expressed by the following equations.

$$X = r \cos (\xi + \Psi)$$

$$Y = r \sin (\xi + \Psi)$$

$$Z = 0$$

Therefore, when the probe is rotated around the X axis by an angle $\Phi$, around the Y axis by an angle $\theta$, around the Z axis by an angle $\Psi$, the coordinates of the point T are expressed by the following equations.

$$Xi = r \cos (\xi + \Psi) \cdot \cos \theta$$

$$Yi = r \sin (\xi + \Psi) \cdot \cos \theta \quad (1)$$

$$Zi = r \sin \xi \cdot \sin \Phi + r \cos \xi \cdot \sin \theta$$

When the probe is moved by the distances dx, dy and dz in the directions of the X axis, the Y axis and the Z axis, the coordinates of the point T are obtained by adding the movement quantities dx, dy and dz to the above coordinates Xi, Yi and Zi, and are expressed by the equations as shown below.

$$X_T = Xi + dx$$

$$Y_T = Yi + dy \quad (2)$$

$$Z_T = Zi + dz$$

Therefore, when two-dimensional tomographic image signals are obtained by setting the probe in a desired position and direction for a subject body, about an image signal of the watch point T of the subject body (reflection strength at the point T), the positions on three-dimensional coordinates surrounding the subject body can be obtained from the above mentioned equations (1) and (2). In this way, when the tomographic image signals are converted to digital signals and three-dimensional coordinate values of each picture element constituting a tomographic image are decided, a plurality of tomographic image signals can be converted to a three-dimensional picture signal and thereby a two-dimensional tomographic image on an arbitrary cross section or a three-dimensional image can be formed.

Next, the explanation on the meaning of scanning the vicinity of the watch point T of the subject body a plurality of times while changing the position and direction of the probe is given in the following.

Figure 2:
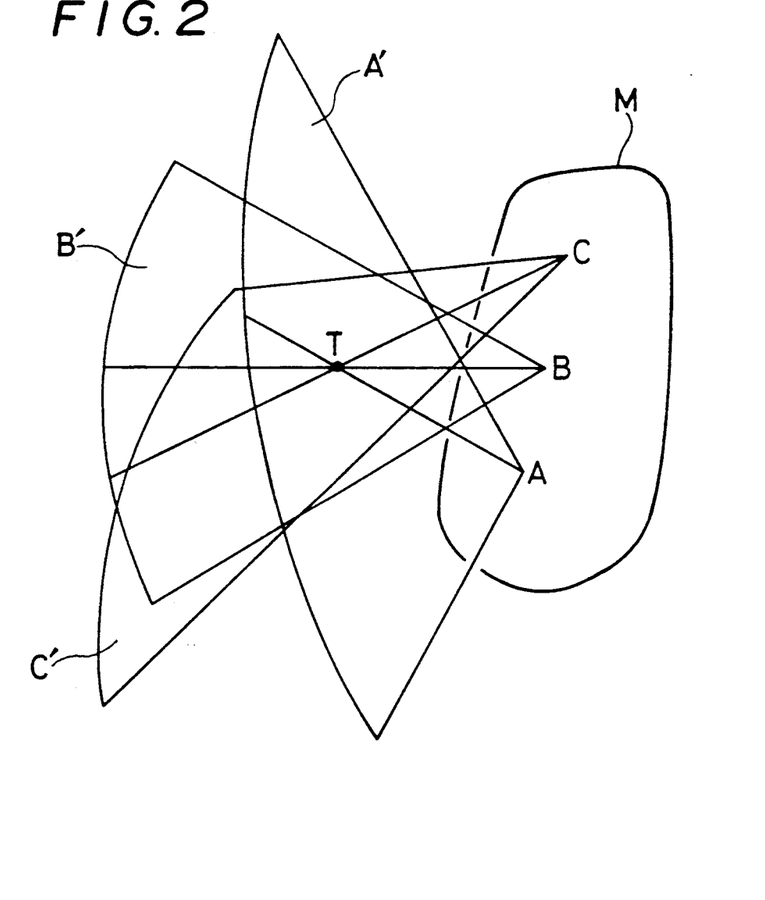
FIG. 2 is an illustrative representation illustrating a scanning plane of an ultrasonic probe for the subject body.

FIG. 2 is an illustrative representation for illustrating the above-mentioned scanning: the probe is applied to a point A on the subject body M and a first scanning is performed on a scanning plane A' including the watch point T; thereafter, the probe is applied to a point B and a second scanning is performed on a scanning plane A' including the watch point T; then the probe is applied to a point C and a third scanning is performed on a plane C' including the watch point T; with the above-mentioned scanning, three tomographic image signals from different positions and directions can be obtained.

In an ideal case where the width of an ultrasonic beam is fine enough, three tomographic image signals are identical, but in an actual case the beam has a certain width and the positions and inclinations of the tomographic planes are different, and the conditions of reflection of the subject body are changed in each case, so that three tomographic image signals do not show the same value. When there is a strong reflection body like a bone in the vicinity of the specific point T of the subject body, the diffraction of an ultrasonic beam occurs and the image is distorted, and so when the positions and inclinations of tomographic planes are different, the obtained tomographic image signals are also different.

If a plurality of tomographic image signals of the same region obtained as mentioned in the above are addition-averaged, a defective part of an image caused by the difference in the scanning direction can be corrected, unnecessary reflection signals can be suppressed, and a better signal can be obtained.

Figure 3:
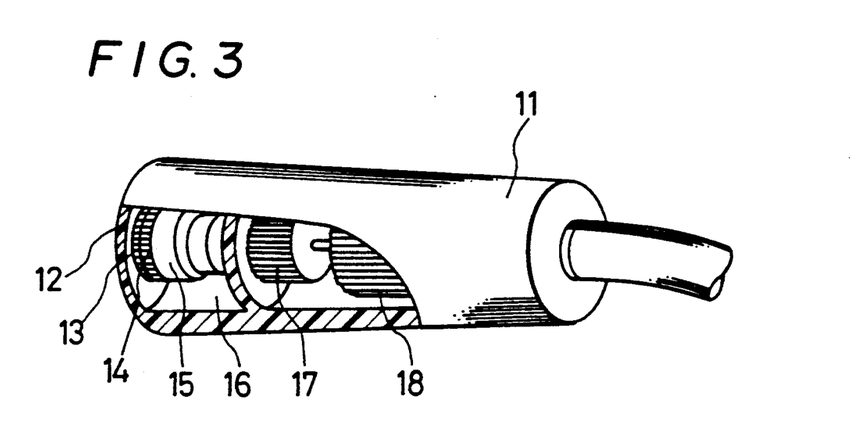
FIG. 3 is a partly cutaway perspective view showing an example of an ultrasonic probe which is suitable for executing the present invention.

FIG. 3 shows the constitution of a well known probe of a sector scanning type to which the present invention can be applied. A probe 11 has an approximately cylindrical form and a sound window 12 is provided on the end of the probe 11. Reference numeral 13 denotes a matching layer, 14 denotes a piezoelectric ceramics and 15 denotes a packing material. The piezoelectric ceramics 14, the matching layer 13 and the packing material 15 are stuck to each other to constitute a vibrator. Reference numeral 16 denotes liquid to be sealed in, 17 denotes an angle detector and 18 denotes a scanning mechanism; the vibrator is driven to be scanned by the scanning mechanism 18 over a specified angle range and the scanning angle $\xi$ (refer to FIG. 1 (a)) is detected with the angle detector 17.

There is a probe of an electronic scanning type other than the one mentioned in the above and both types can be used.

Figure 4:
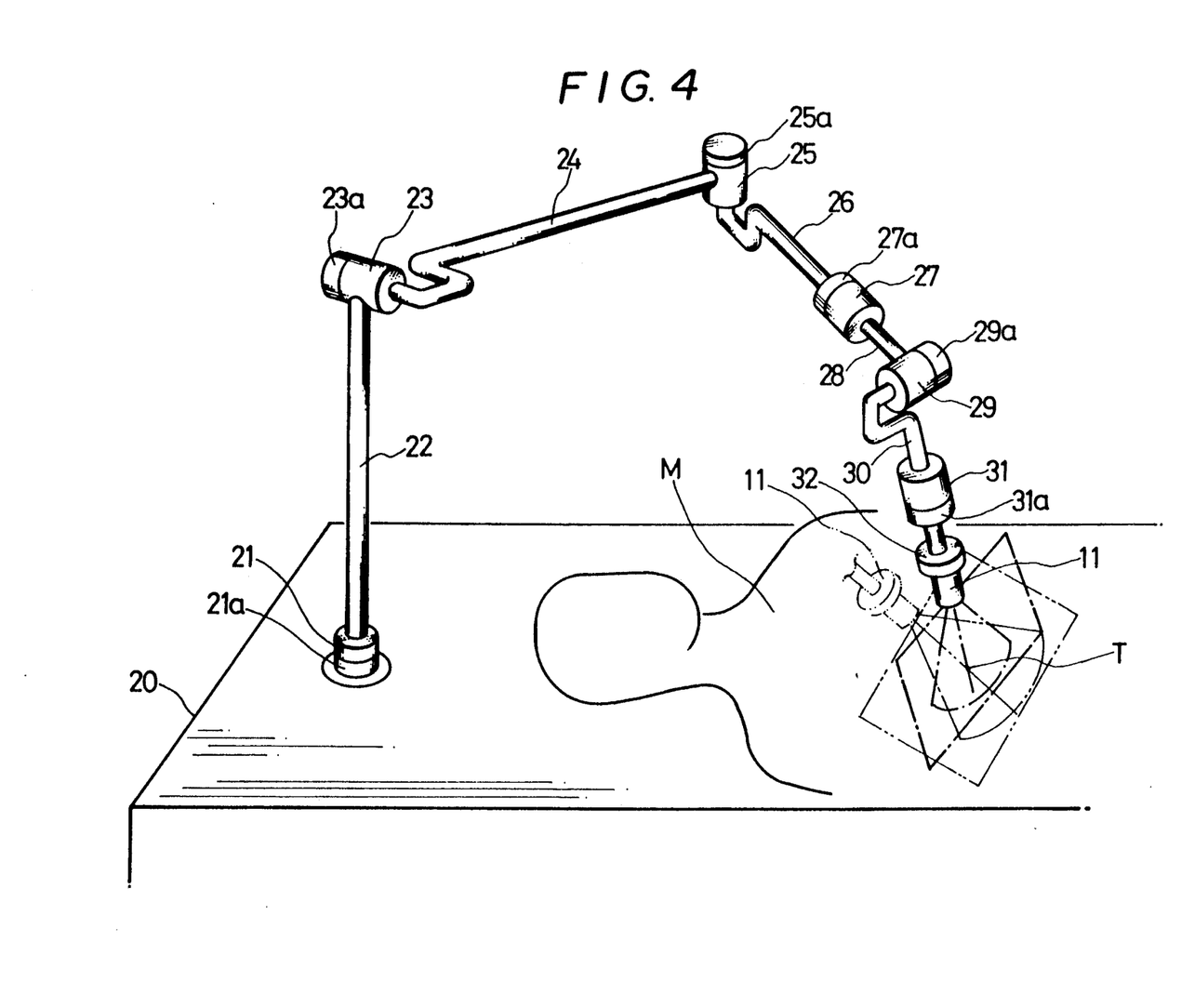
FIG. 4 is a perspective view showing an example of an articulated arm for supporting the probe.

The probe 11 is, as shown in FIG. 4, fixed on the tip of an articulated arm having at least 6 degrees of freedom, and is so constituted that it can set the vibrator surface of a probe in the arbitrary position of a subject body.

Reference numerals 21, 23, 25, 27, 29 and 31 shown in FIG. 4 are freely rotatable articulations; the articulation 21 is fixed on an inspection table 20 or on a bed and it is the origin of three-dimensional coordinates surrounding the subject body. The articulations 21 and 23 are connected by an arm 22, the articulations 23 and 25 are connected by an arm 24, the articulations 25 and 27 are connected by an arm 26, the articulations 27 and 29 are connected by an arm 28, and the articulations 29 and 31 are connected by an arm 30; a probe supporting part 32 is fixed on the articulation 31. Individual articulations are provided respectively with conventional encoders 21a, 23a, 25a, 27a, 29a and 31a, and the detected rotation angle of each of these articulations is inputted into a position-direction detector which is explained later.

The position-direction detector operates and outputs coordinate values (dx, dy and dz) which express the position of the probe and the angles ($\Phi$, $\theta$ and $\Psi$) which express the direction of the probe for the origin of a three-dimensional coordinate system from the rotation angles detected by the encoders provided on individual articulations and the known lengths of individual arms.

Figure 5:
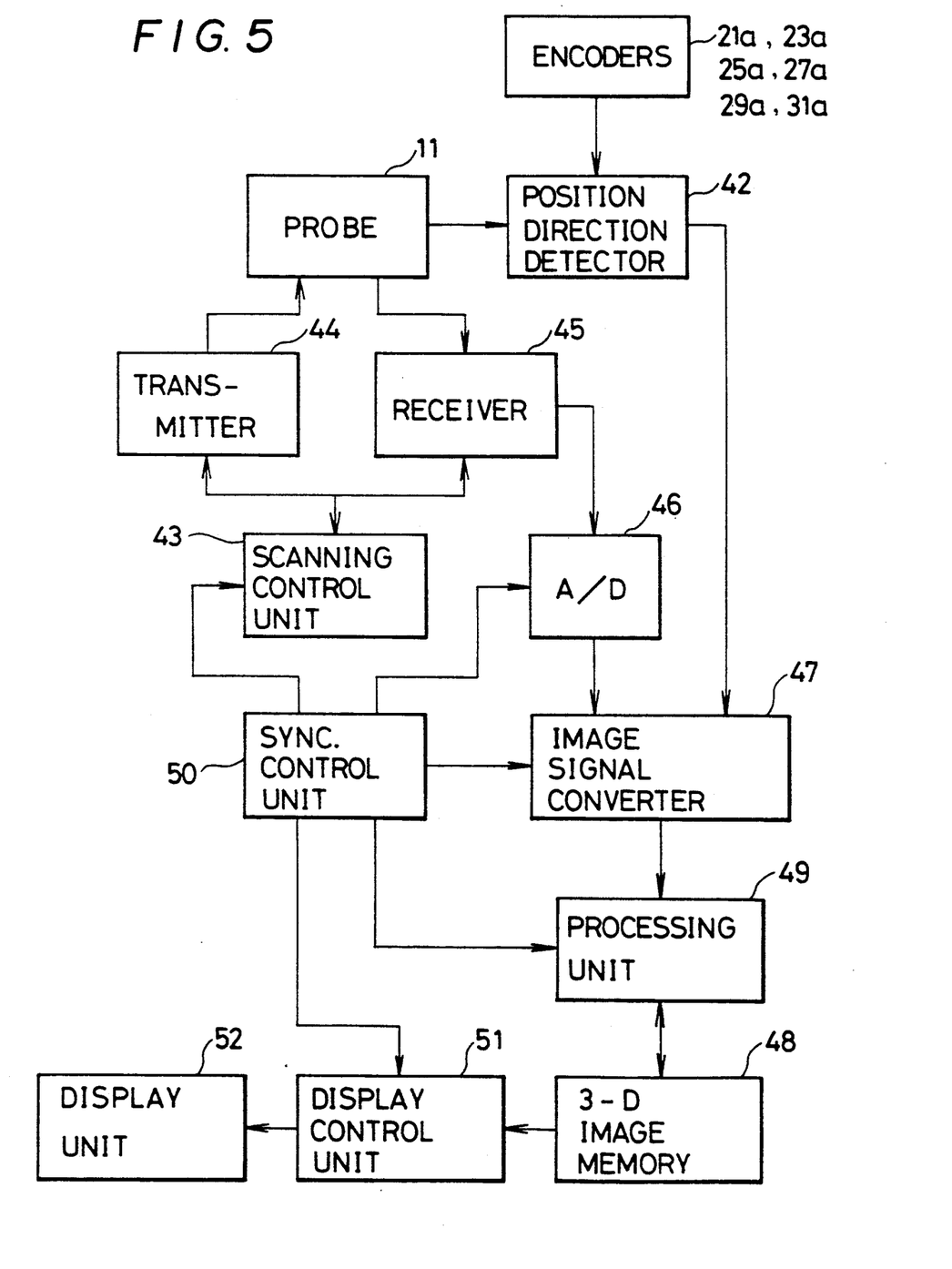
FIG. 5 shows a circuit block diagram of a first embodiment of an ultrasonic diagnostic device according to the present invention.

FIG. 5 is a block diagram showing the constitution of a first embodiment of an ultrasonic diagnostic device according to the present invention in which: reference numeral 11 denotes a probe; reference numeral 42 denotes a position-direction detector for detecting the position and direction of the probe for the origin of a three-dimensional coordinate system surrounding a subject body when the probe is set on the subject body; reference numeral 43 designates a scanning control unit which excites the probe in driving a transmitter 44 to transmit ultrasonic pulses for the subject body and receives with a receiver the reflected waves detected with the probe, under the control of a synchronous control signal outputted from a synchronous control unit 50. In the figure, reference numeral 46 designates an A/D converter which converts the tomographic image analog signal received with the receiver 45 to a digital signal, and in this process the tomographic image is decomposed to many picture elements; reference numeral 47 designates an image signal converter which inputs the A/D converted tomographic image signal and a position-direction signal of the probe detected with the position-direction detector 42 under the control of the synchronous control unit 50, and gives the position-direction signal of the probe to the two-dimensional tomographic image signal detected with the probe 11 to decide the position of the signal in the three-dimensional coordinate system surrounding the subject body for converting the two-dimensional tomographic image signal to a three-dimensional image signal. In the figure, reference numeral 48 designates a three-dimensional image memory which has a memory area corresponding to each picture element of an image signal expressed in three-dimensional coordinates; reference numeral 49 designates a processing unit which reads out an image signal in the memory area corresponding to the designated three-dimensional coordinates from the three-dimensional image memory, and operates an addition-average of the above image signal and the image signal having corresponding three-dimensional coordinates outputted from the image signal converter, and again stores the operated image signal into the corresponding memory area of the three-dimensional image memory, under the control of the synchronous control unit 50. In the figure, reference numeral 51 denotes a display control unit being operated under the control of the synchronous control unit 50, and it reads out an image signal of a necessary part from the three-dimensional memory in receiving a signal expressing the kind of a display image (distinction between a two-dimensional tomographic image and a three-dimensional image and so on) and a signal designating a region which are inputted from the outside, and after the image edition, the signal is outputted to the display unit 52.

The explanation on the operation of the device will be given in the following.

At first, the probe 11 is set in a first position and direction A on the subject body M for scanning (see FIG. 2). The obtained two-dimensional tomographic image signal is converted to a digital signal by the A/D converter 46 and then inputted into the image signal converter 47. A signal Bi expressing the reflection strength, a scanning deviation angle $\xi$ and an echo time, that is, a signal showing the depth r (see FIG. 1) are contained in this signal. The signals expressing the positions (dx, dy and dz) of the probe for the origin of a three-dimensional coordinate system surrounding the subject body and the inclination angles ($\Phi$, $\theta$ and $\Psi$) for the axes X, Y and Z are outputted from the position-direction detector 42, and the signals are inputted into the image signal converter 47. The image signal converter 47 calculates the positions in the three-dimensional coordinates of the signals Bi expressing the reflection strength based on the equations (1) and (2) which are explained previously, and the signals are converted into three-dimensional image signals. These processings are executed on all the picture elements constituting a two-dimensional tomographic image, so that the first tomographic image obtained by scanning the subject body is formed as an aggregate of the picture elements in the space of a three-dimensional coordinate system. In the processing unit 49, addition-average of the three-dimensional image signals which are obtained and the image signals which are stored in the three-dimensional image memory 48 are operated; in the case of a first scanning, since the contents of the three-dimensional image memory 48 are 0, the image signals obtained in the first scanning are stored in memory areas corresponding to each of the coordinates.

In the scanning on and after the second time, either of the position or the direction of the probe, or both of them are changed little by little from those of the previous time. The obtained two-dimensional tomographic image signals are processed in the similar way to the first time scanning and converted into three-dimensional image signals. In the processing part 49, addition-average of the obtained three-dimensional image signals and the image signals stored in the three-dimensional image memory 48 are operated, and the operated signal is again stored in a memory area corresponding to respective coordinates.

As clearly understood in referring to FIG. 2, image signals stored in the three-dimensional image memory express a plurality of tomographic images of different positions and directions in the space of a three-dimensional coordinate system, but concerning the watch point T, the image signal is an addition-average of a plurality of image signals.

In the above description, the watch point is assumed to be a single point to facilitate understanding, but when the scannings of a plurality of times are performed in moving the position and the direction of the probe for the subject body little by little, a plurality of image signals for a plurality of the watch points on the subject body can be obtained, so that there can be eventually stored in the three-dimensional image memory a high quality three-dimensional image signal which is not influenced by the reflection or diffraction of ultrasonic waves caused by the state of a tissue of the subject body.

Figure 6:
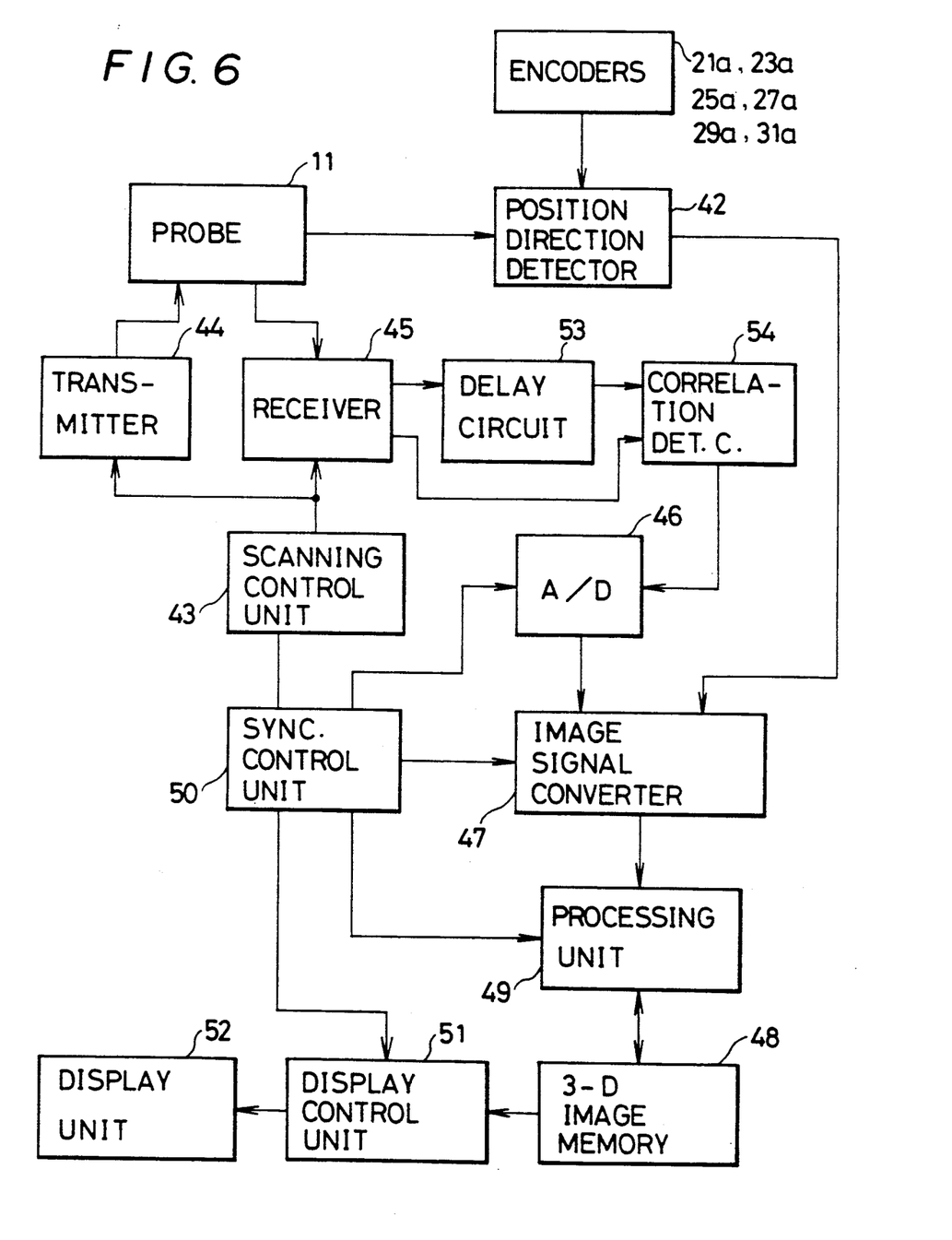
FIG. 6 shows a circuit block diagram of a second embodiment of an ultrasonic diagnostic device according to the present invention.

FIG. 6 is a block diagram showing the constitution of a second embodiment of an ultrasonic diagnostic device according to the present invention. It is a device to display a pulse tract image of the subject body as a two-dimensional or three-dimensional image, and a Doppler tomographic image signal is used as a two-dimensional tomographic image signal.

The different point from the circuit block diagram in the first embodiment shown in FIG. 5 is that a delay circuit 53 and a correlation detection circuit 54 are provided between the receiver 45 and the A/D converter 46 to obtain a Doppler tomographic image signal; with this arrangement, only the pulse tract image signal having movement caused by blood flow etc. can be taken out by detecting the phase differences of tomographic image signals which are successively received. A three-dimensional image of the pulse tract image can be obtained in processing the obtained pulse tract image signals with the following circuits as shown in FIG. 5, and in converting them to three-dimensional image signals.

When the three-dimensional image of the pulse tract image is displayed in a display device if coloring is made in proportion to the detected phase difference, that is, the blood velocity and the three-dimensional image of the tissue is simultaneously displayed, the colored pulse tract image is sharply outlined against the three-dimensional image of the tissue; it helps understand anatomical knowledge.

To scan the subject body while changing the position or direction of the probe, several kinds of methods are considered such as a method in which the probe is manually handled, a method in which the scanning mechanism is moved on guide rails provided in the directions of X, Y and Z axes, or a method in which a robot is used; the present invention can be applied to the manual scanning method and also to the mechanical scanning method, specially in the case of the latter, if tomographic images are photographed automatically utilizing the deviation quantity of positions and the changing quantity of angles outputted from the position-direction detector, for example, if images are taken in every change of 5 mm or 1 degree, a plurality of tomographic images can be efficiently photographed.

As described in the above according to the present invention, an image signal is created by synthesizing a plurality of image signals concerning one and the same region of a subject body in a space of a three-dimensional coordinate system from two-dimensional tomographic image signals obtained by scanning the subject body from a plurality of different positions and directions and the synthesized image signal is stored in a three-dimensional image memory, so that the influence of reflection or diffraction of ultrasonic waves which occurs in scanning from a specific position or a direction depending on the conditions of the tissue of the subject body is removed and a high quality three-dimensional image signal can be obtained. When a two-dimensional Doppler tomographic image signals are inputted in place of the two-dimensional tomographic image signals and the similar processes to the above ones are executed, a three-dimensional pulse tract image signal can be obtained.

Single every picture element which constitutes a three dimensional image signal stored in the three-dimensional image memory has its own definite coordinates, when an arbitrary section is decided in designating coordinates, a tomographic image of the section can be displayed in a display device. It is also possible to display the image in the display device as a three-dimensional image.

What is claimed is:

1. An ultrasonic diagnostic device having an ultrasonic probe and a probe driving means for transmitting ultrasonic pulses to a subject body, for obtaining a plurality of two-dimensional tomographic image signals by detecting the reflected pulses and for synthesizing a plurality of the two-dimensional tomographic image signals to form a three-dimensional image signals comprising:

(1) a probe supporting means for freely setting the position and the direction of the radiating surface of a pulse beam radiated from said ultrasonic probe in a three-dimensional space surrounding the subject body;

(2) a probe position-direction detection means for detecting the position and the direction of the radiating surface of the pulse beam in reference to the origin of three-dimensional coordinates for identifying the three-dimensional space surrounding the subject body;

(3) an image signal conversion means for A/D converting the two-dimensional tomographic image signals of the subject body detected with said probe to discompose the signals into picture elements; for forming a signal to identify the position in the three-dimensional coordinates concerning each picture element composing the image based on the signal showing the position and the direction of said probe; and for giving an identification signal to each picture element;

(4) a three-dimensional image memory means comprising a memory area for a plurality of picture element signals corresponding to the positions in the three-dimensional space to be identified by the three-dimensional coordinates;

(5) an image signal processing means for operating two kinds of signals with an addition-averaged method and for storing the operation results again into the memory area of the same coordinates as those wherein the signals had been stored; one of the signals being the picture element signals, composing the two-dimensional tomographic images, leaving the identified positions in a three-dimensional coordinate system being identified by said image signal conversion means; the other one of the signals being the picture element signals read out from said three-dimensional image memory means storing them in corresponding coordinate positions.

2. An ultrasonic diagnostic device according to claim 1 wherein said probe supporting means comprises an articulated arm having at least 6 degrees of freedom.

3. An ultrasonic diagnostic device according to claim 2 wherein said probe position-direction detection means comprises angle detection encoders on the articulation parts and an operation circuit for operating the position and direction of the radiating surface of the pulse beam radiated from said probe, based on a known arm length and angle signals outputted from said encoders.

4. An ultrasonic diagnostic device according to claim 1 wherein the two-dimensional tomographic image signal is a two-dimensional Doppler tomographic image signal.

5. An ultrasonic diagnostic device for synthesizing a three-dimensional image signal from a plurality of two-dimensional tomographic image signals comprising:

an ultrasonic probe and a probe driving means for transmitting ultrasonic pulses to a subject body for obtaining a plurality of analog, two-dimensional tomographic image signals by detecting the reflected pulses;

a probe supporting means for freely setting the position and the direction of the radiating surface of a pulse beam radiated from said ultrasonic probe in a three-dimensional space surrounding the subject body;

a probe position-direction detection means for detecting the position and the direction of the radiating surface of the pulse beam in reference to an origin of the three-dimensional space surrounding the subject body;

an image signal conversion means for converting the analog, two-dimensional tomographic image signals of the subject body detected with said probe into digital picture elements;

means for forming a position signal in three-dimensional coordinates for each picture element composing the image based on the probe position and direction;

a three-dimensional image memory means having a memory area for each of a plurality of picture element signals identified by the three-dimensional coordinates, and;

an image signal processing means for receiving the three-dimensional picture element signals of a probe scan from the image signal conversion means, combining each received picture element signal with a corresponding three-dimensional picture element signal previously stored in the memory means, and storing the combined picture element signal in the memory means to form a three-dimensional image which is updated with each probe scan.

6. The ultrasonic diagnostic device of claim 5 wherein said probe supporting means comprises an articulated arm having at least 6 degrees of freedom.

7. The ultrasonic diagnostic device of claim 5 wherein said image signal processing means combines said picture element signal by addition-averaging.

* * * * *